(12) United States Patent
Jang et al.

(10) Patent No.: US 10,399,935 B2
(45) Date of Patent: Sep. 3, 2019

(54) METHOD FOR PRODUCING 3-MERCAPTOPROPIONIC ACID, AND METHODS USING SAME FOR PRODUCING CARBOXYLIC ACID ESTER COMPOUND HAVING MERCAPTO GROUP AND THIOURETHANE-BASED OPTICAL MATERIAL

(71) Applicant: KOC SOLUTION CO., LTD., Daejeon (KR)

(72) Inventors: Dong Gyu Jang, Daejeon (KR); Soo Gyun Roh, Daejeon (KR)

(73) Assignee: KOC SOLUTION, LTD., Yuseong-Gu, Daejeon (KR)

( * ) Notice: Subject to any disclaimer, the term of this patent is extended or adjusted under 35 U.S.C. 154(b) by 0 days.

(21) Appl. No.: 15/737,923

(22) PCT Filed: Jun. 17, 2016

(86) PCT No.: PCT/KR2016/006433
§ 371 (c)(1),
(2) Date: Dec. 19, 2017

(87) PCT Pub. No.: WO2016/204547
PCT Pub. Date: Dec. 22, 2016

(65) Prior Publication Data
US 2018/0179154 A1 Jun. 28, 2018

(30) Foreign Application Priority Data

Jun. 19, 2015 (KR) .................. 10-2015-0087758

(51) Int. Cl.
| | | |
|---|---|---|
| *C08G 18/00* | (2006.01) | |
| *C08G 61/04* | (2006.01) | |
| *C07C 319/12* | (2006.01) | |
| *C07C 319/04* | (2006.01) | |
| *C07C 319/26* | (2006.01) | |
| *C08L 81/00* | (2006.01) | |
| *G02B 1/04* | (2006.01) | |
| *C08G 18/38* | (2006.01) | |
| *C08G 18/72* | (2006.01) | |
| *C08G 18/73* | (2006.01) | |
| *C08G 18/75* | (2006.01) | |

(52) U.S. Cl.
CPC .......... *C07C 319/12* (2013.01); *C07C 319/04* (2013.01); *C07C 319/26* (2013.01); *C08G 18/3876* (2013.01); *C08G 18/722* (2013.01); *C08G 18/73* (2013.01); *C08G 18/755* (2013.01); *C08L 81/00* (2013.01); *G02B 1/04* (2013.01); *G02B 1/041* (2013.01)

(58) Field of Classification Search
CPC ... C07C 319/12; C07C 319/04; C07C 321/14; C07C 319/26; C08G 18/722; C08G 18/755; C08G 18/73; C08G 18/3876; G02B 1/041; G02B 1/04; C08L 81/00
USPC ........................................ 528/80, 44; 520/1
See application file for complete search history.

(56) References Cited

FOREIGN PATENT DOCUMENTS

| | | | |
|---|---|---|---|
| JP | 58-198460 | * | 11/1983 |
| JP | 06-145138 | | 5/1994 |
| JP | 07-2911921 | | 11/1995 |
| KR | 10-2008-0090548 | | 10/2008 |
| KR | 10-2013-0087447 | | 8/2013 |
| WO | WO-2013112028 A1 | * | 8/2013 ........... C07C 319/04 |

OTHER PUBLICATIONS

Yotsukaichi, JP 58-198460 Machine Translation, Nov. 18, 1983 (Year: 1983).*
Yotsukaichi, JP 58-198460 Abstract, Nov. 18, 1983 (Year: 1983).*
Kim et al, WO 2013/112028 Machine Translation, Aug. 1, 2013 (Year: 2013).*
International Search Report pct/KR2016/006433, Oct. 11, 2016 (Year: 2016).*
International Search Report for PCT/KR2016/006433 dated Nov. 9, 2016 (5 pages).

* cited by examiner

*Primary Examiner* — Jessica Whiteley
(74) *Attorney, Agent, or Firm* — Susan Paik, Esq.

(57) ABSTRACT

A method for producing 3-mercaptopropionic acid and methods using same for producing a carbonic acid ester compound having a mercapto group and a thiourethane-based optical material. The present invention improves a process during the production of 3-mercaptopropionic acid, significantly increases yield, and reduces the temperature and time during vacuum distillation, thereby preventing the destruction of a product and significantly increasing productivity. The present invention allows high-purity 3-mercaptopropionic acid having an excellent color to be finally yielded; accordingly, by using same, a high-purity carbonic acid ester compound having an excellent color and a mercapto group can be inexpensively obtained. A thiourethane-based polymeric composition and a thiourethane-based optical material obtained by polymerizing same can likewise be inexpensively obtained by using said carbonic acid ester compound. Such carbonic acid ester compound can be used for the production of inexpensive thiourethane optical lenses; consequently, inexpensive optical lenses having an excellent color can be obtained.

8 Claims, No Drawings

METHOD FOR PRODUCING 3-MERCAPTOPROPIONIC ACID, AND METHODS USING SAME FOR PRODUCING CARBOXYLIC ACID ESTER COMPOUND HAVING MERCAPTO GROUP AND THIOURETHANE-BASED OPTICAL MATERIAL

TECHNICAL FIELD

The present invention relates to a method for preparing 3-mercaptopropionic acid and methods for producing, using the same, a carboxylic acid ester compound having a mercapto group and a thiourethane-based optical lens.

BACKGROUND ART

Mercaptocarboxylic acid (mercaptopropionic acid) is used for synthetic resins because it is suitable as a cross-linking agent of acrylic acid ester polymers and a curing agent of epoxy resins. In particular, a variety of carboxylic acid ester compounds can be synthesized by esterification reaction of such mercaptocarboxylic acid (mercaptopropionic acid) with alcohols.

U.S. Pat. No. 5,008,432 discloses preparation of 3-mercaptopropionic acid by adding hydrogen sulfide to an unsaturated compound such as methacrylate or acrylic acid. Addition of the hydrogen sulfide is carried out in the presence of a basic catalyst selected from magnesium oxide and an anion exchange resin. The resin was selected from those containing tertiary amines as functional groups and those containing quaternary ammonium hydroxides as functional groups. However, this method involves adding hydrogen sulfide to acrylic acid to convert the acrylic acid into 3-mercaptopropionic acid ($HSCH_2CH_2COOH$), thus making the process very complicated.

Korean Patent Laid-open No. 1998-024803 discloses a method for synthesizing 3-mercaptopropionic acid by addition reaction between acrylic acid and hydrogen sulfide. Like U.S. Pat. No. 5,008,432, the reaction is carried out in the presence of a solid support having a guanidine functional group which does not contain a hydrogen directly bonded to a nitrogen atom, instead of using amine.

Korean Patent Laid-open No. 1998-024803 discloses synthesis of 3-mercaptopropionic acid at a high conversion proportion and high selectivity through addition reaction with acrylic acid and hydrogen sulfide in the presence of a solid support having a basic functional group. However, the drawback of complicated preparation process remains.

CN Patent No. 101125827A discloses a method for converting thiodipropionic acid (dimer) into 3-mercaptopropionate (polymer). This method requires relatively vigorous reaction conditions due to acid treatment with strong acid and iron, and thus has problems of undesired composition of products and occurrence of by-products under such conditions.

In addition, Korean Patent No. 10-0350658 discloses a preparation method to easily treat 3-mercaptopropionitrile and 3-mercaptopropionic acid. The method of the present invention includes reacting with alkali hydrosulfide (alkali hydrogen sulfide) in the presence of an alkali hydroxide using thiodipropionitrile as a starting material to produce 3-mercaptopropionitrile at a high yield. The resulting nitrile is acidized with strong acid or saponified to obtain the desired mercaptopropionic acid at a high yield. With this invention, 3-mercaptopropionitrile and 3-mercaptopropionic acid can be obtained at high yields without incorporating dithiodipropionitrile and dithiodipropionic acid. However, this method should include preparing thiodipropionitrile (dimer) using acrylonitrile and sodium hydrosulfide, adding sodium hydrosulfide and sodium hydroxide thereto to prepare 2-sodium cyanoethanethiolate (monomer), and refluxing the 2-sodium cyanoethanethiolate in the presence of strong acid (hydrochloric acid) to convert nitrile into a carboxylic group. This causes many problems of complicated reaction step, difficulty in preparation, low yield of products resulting from conversion of the nitrile into the carboxylic group under the condition of refluxed hydrochloric acid, without separating 3-mercaptopropionitrile, and a great amount of 3-mercaptopropionitrile remains unreacted.

In order to solve these conventional problems, Korean Patent Laid-open No. 10-2013-0087447 provides a method for preparing 3-mercaptopropionic acid that eliminates the necessity of the process of obtaining 3-mercaptopropionitrile from thiodipropionitrile using thiodipropionitrile (dimer) with sodium hydrosulfide and sodium hydroxide. In accordance with this method, acrylonitrile is reacted with sodium hydrosulfide to obtain 2-sodium cyanoethanethiolate, the 2-sodium cyanoethanethiolate is neutralized with an acid, layer-separation is conducted to obtain 3-mercaptopropionitrile, the 3-mercaptopropionitrile is converted into 3-mercaptopropionic acid by addition of an acid and reflux, and the 3-mercaptopropionic acid is distilled under reduced pressure to obtain 3-mercaptopropionic acid. This method is a simple and economically efficient process, in that 3-mercaptopropionitrile involved in preparation of less dimer is obtained, and provides a higher yield compared to the aforementioned other methods. However, this method entails considerable yield loss and degradation of products resulting from high-temperature treatment in the process of obtaining 3-mercaptopropionitrile, and converting 3-mercaptopropionitrile into 3-mercaptopropionic acid by acid addition and distilling under reduced pressure. Therefore, there is a need for improvement that can enhance a yield while distilling products under reduced pressure at a lower temperature.

LISTING OF PATENT DOCUMENTS (Patent Document 1) U.S. Pat. No. 5,008,432
(Patent Document 2) KR Patent Laid-open No. 1998-024803
(Patent Document 3) CN Patent No. 101125827A
(Patent Document 4) KR Patent No. 10-0350658
(Patent Document 5) KR Patent Laid-open No. 10-2013-0087447

SUMMARY OF THE INVENTION

Technical Problem

Therefore, the present invention has been made in order to solve the conventional problems described above and it is one object of the present invention to provide a method for preparing 3-mercaptopropionic acid that includes reacting acrylonitrile with sodium hydrosulfide to obtain 2-sodium cyanoethanethiolate, neutralizing 2-sodium cyanoethanethiolate with an acid to obtain 3-mercaptopropionitrile, and adding an acid thereto and distilling under reduced pressure to obtain 3-mercaptopropionic acid, wherein the method is a new method that can significantly increase a yield while preventing degradation of products by reducing the temperature in the process of distilling under reduced pressure to obtain the final product. In addition, the present invention provides 3-mercaptopropionic acid with excellent purity and color at a low cost by preparing 3-mercaptopropionic acid at a high yield and purity by an easy and simple process.

In addition, it is another object of the present invention to prepare a carboxylic acid ester compound having a mercapto group with excellent purity and color at a low cost using the 3-mercaptopropionic acid thus obtained.

In addition, it is another object of the present invention to provide an optical material with excellent color and quality at a low cost using the carboxylic acid ester compound having a mercapto group thus obtained, in particular, to produce a high-quality low-cost urethane-based optical lens with high quality.

Technical Solution

In accordance with the present invention, the above and other objects can be accomplished by the provision of a method for preparing 3-mercaptopropionic acid including (a) reacting acrylonitrile with sodium hydrosulfide to obtain 2-sodium cyanoethanethiolate, (b) neutralizing the 2-sodium cyanoethanethiolate with an acid to obtain 3-mercaptopropionitrile, and (c) adding an acid to the 3-mercaptopropionitrile, refluxing the resulting mixture and distilling the resulting reaction solution under reduced pressure to obtain 3-mercaptopropionic acid, wherein the step (c) includes adding the acid to the 3-mercaptopropionitrile and refluxing the resulting mixture to convert the 3-mercaptopropionitrile into 3-mercaptopropionic acid, adding one or more organic solvents of n-butyl acetate and methyl isobutyl ketone to the 3-mercaptopropionic acid to prepare a mixture solution, neutralizing the mixture solution with aqueous ammonia, and filtering the resulting solution to remove an aqueous layer as a lower layer and allow an organic layer as an upper layer to be left, and removing the solvent under reduced pressure from the organic layer and then distilling under reduced pressure to obtain 3-mercaptopropionic acid.

In addition, in another aspect of the present invention, provided is a method for preparing a carboxylic acid ester compound having a mercapto group including esterifying the 3-mercaptopropionic acid obtained by the method described above with a compound having a monovalent or higher alcohol group to obtain the carboxylic acid ester compound having a mercapto group.

In addition, in another aspect of the present invention, provided is a method for preparing a thiourethane-based polymerizable composition including mixing the carboxylic acid ester compound having a mercapto group obtained by the method described above with a polyiso(thio)cyanate compound to prepare the polymerizable composition.

In addition, in another aspect of the present invention, provided is a method for for producing a thiourethane-based optical material including polymerizing the polymerizable composition obtained by the method described above to obtain the optical material.

In addition, in another aspect of the present invention, provided is a thiourethane-based optical material obtained by the method described above, wherein the optical material includes an optical lens such as a lens for eyeglasses.

DETAILED DESCRIPTION OF THE INVENTION

The present invention can greatly increase a yield to 10% or higher and at the same time by enhancing the process of obtaining 3-mercaptopropionic acid by addition of an acid after obtaining 3-mercaptopropionitrile, and can significantly enhance productivity and prevent degradation of products by lowering the temperature during distillation under reduced pressure and shortening the distillation time. The present invention can greatly enhance yield and productivity in spite of carrying out an easy and simple process which is not difficult to perform. This results in an effect of greatly reducing the total production cost of lens through reduction in costs for producing thiol compounds in the field of an optical material, in particular, a lens for eyeglasses, in which reduction in production costs is considered to be an important task. In addition, since the 3-mercaptopropionic acid produced according to the present invention has excellent purity and color, it is possible to obtain a carboxylic acid ester compound having a mercapto group with excellent purity and color at a low cost using the same, as well as a thiourethane-based polymerizable composition at a low cost using the carboxylic acid ester compound and a thiourethane-based optical lens obtained by polymerizing the same. The carboxylic acid ester compound according to the present invention can be used for production of, in particular, low-cost thiourethane optical lenses, and as a result, a cheap optical lens with excellent color can be obtained.

Hereinafter, the present invention will be described in more detail.

The method for preparing 3-mercaptopropionic acid of the present invention includes: (a) reacting acrylonitrile with sodium hydrosulfide to obtain 2-sodium cyanoethanethiolate; (b) neutralizing the 2-sodium cyanoethanethiolate with an acid to obtain 3-mercaptopropionitrile; and (c) adding an acid to 3-mercaptopropionitrile, refluxing the 3-mercaptopropionitrile and distilling the resulting reaction solution with reduced pressure to obtain 3-mercaptopropionic acid, and is preferably depicted by the following Reaction Scheme 1. Hereinafter, respective processes will be described in detail.

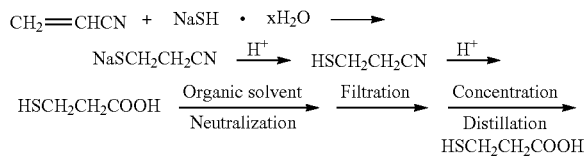

[Reaction Scheme 1]

(a) Obtaining 2-sodium Cyanoethanethiolate

Acrylonitrile is reacted with sodium hydrosulfide to obtain 2-sodium cyanoethanethiolate. The acrylonitrile and sodium hydrosulfide are preferably reacted in a molar ratio of 1:0.9 to 1:1.5. In a conventional method, an excess of alkali hydrosulfide was added to acrylonitrile in order to facilitate reaction. Korean Patent No. 10-0350658 discloses reaction of acrylonitrile with an excess of sodium hydrosulfide and use of an excess of a base and sodium hydrosulfide to convert thiodipropionitrile formed by this reaction into 3-mercaptopropionitrile. However, the present invention uses of acrylonitrile and sodium hydrosulfide in an appropriate ratio to obtain 3-mercaptopropionitrile while reducing preparation of thiodipropionitrile as a dimer. By doing so, 3-mercaptopropionitrile can be obtained at a high purity and a high yield without conducting a process of using an excess of base and sodium hydrosulfide to convert thiodipropionitrile into 3-mercaptopropionitrile. In Reaction Scheme shown above, more preferably, the acrylonitrile is reacted with sodium hydrosulfide in a molar ratio of 1:0.9 to 1:1.2, particularly preferably in a molar ratio of 1:1. At this time, the acrylonitrile and sodium hydrosulfide are preferably reacted at a temperature within the range of higher than 30° C. and lower than 80° C., more preferably within the range of higher than 40° C. and lower than 60° C., in order to prepare 3-mercaptopropionitrile at a high yield, while preparing almost no by-products such as dimers within the molar ratio.

(b) Obtaining 3-mercaptopropionitrile

The 2-sodium cyanoethanethiolate obtained by the reaction described above is neutralized with an acid to obtain 3-mercaptopropionitrile. At this time, preferably, after neutralization of 2-sodium cyanoethanethiolate by addition of an acid, layer-separation is conducted to obtain 3-mercaptopropionitrile. More preferably, an excess of hydrochloric acid is added to a reactor containing 2-sodium cyanoethanethiolate to convert the 2-sodium cyanoethanethiolate into 3-mercaptopropionitrile. At this time, the neutralization is preferably carried out by dropping the temperature of the reactor to about 10° C. and dropwise adding concentrated hydrochloric acid thereto at a temperature of 10° C. or less while stirring. After dropwise addition, stirring is stopped, nitrile as the supernatant layer is layer-separated and the aqueous layer as a lower layer is removed. As a result, only the organic layer as an upper layer is obtained. More preferably, 3-mercaptopropionitrile can be obtained by effective layer-separation when a 1.2-times excess of hydrochloric acid with respect to an equivalent of an acid for neutralization is used.

(c) Obtaining 3-mercaptopropionic acid

After addition of an acid to the 3-mercaptopropionitrile obtained by the reaction and reflux, distillation under reduced pressure is conducted to obtain 3-mercaptopropionic acid. Preferably, the present process includes adding an acid to the 3-mercaptopropionitrile, followed by refluxing to convert the 3-mercaptopropionitrile into 3-mercaptopropionic acid; cooling the 3-mercaptopropionic acid, adding a polar organic solvent thereto to prepare a mixture solution, neutralizing the mixture solution with ammonia, filtering the resulting solution and removing the aqueous layer as the lower layer to allow only the organic layer as the upper layer to remain; removing the solvent under reduced pressure from the organic layer and distilling the residue under reduced pressure at 110° C. to 130° C. to obtain 3-mercaptopropionic acid.

First, the step of converting 3-mercaptopropionitrile into 3-mercaptopropionic acid is preferably carried out by slowly adding concentrated hydrochloric acid to the organic layer containing the 3-mercaptopropionitrile obtained by the process described above while stirring, and proceeding reaction at about 60° C. for about one hour and then refluxing at 110 to 130° C. for 10 to 15 hours to convert into 3-mercaptopropionic acid. As the amount of acid added increases, the speed of conversion into 3-mercaptopropionic acid increases. Accordingly, a slight excess of acid is preferably added. When the post-process is conducted without neutralization with a base, by-products of reaction of an organic solvent and mercaptopropionic acid are obtained due to the acid catalyst.

Since the 3-mercaptopropionic acid thus prepared is present in the reaction solution in the form of a mixture with water and an organic solvent, layer-separation of the reaction solution is impossible and it is difficult to remove water from the reaction solution. In the present step, the reaction solution containing 3-mercaptopropionic acid produced during the previous step is cooled, at least one organic solvent selected from n-butyl acetate and methyl isobutyl ketone is added thereto and the resulting mixture is neutralized with ammonia and then filtered. As a result, the mixture is separated into an aqueous layer as the lower layer and an organic layer and thus only the organic layer as the upper layer can be left by removing the aqueous layer. When cooling the reaction solution, the temperature is preferably lowered to 15° C. or less, more preferably to about 5 to 15° C., particularly preferably to about 10° C. As the temperature of the reaction solution decreases, selective solubility to n-butyl acetate or the like increases and layer-separation is facilitated. 3-mercaptopropionic acid has low selective solubility to methylene chloride, methyl ethyl ketone, chloroform and the like, which are generally used as organic solvents, no great solubility difference from water and is difficult to extract due to low fractionation factor and is difficult to separate by filtering. In the present invention, these problems can be solved by using n-butyl acetate or methyl isobutyl ketone, particularly preferably, n-butyl acetate. n-butyl acetate can dissolve the carboxylic functional group of 3-mercaptopropionic acid, but is a polar organic solvent which is immiscible with water and has high solubility to 3-mercaptopropionic acid. As such, when n-butyl acetate is added after dropping the temperature of the reaction solution, almost 100% of 3-mercaptopropionic acid in the reaction solution is selectively dissolved in n-butyl acetate and layer-separation between the aqueous layer and the n-butyl acetate layer is possible, which allows for removal of water.

As such, after the water is removed and only the organic layer containing 3-mercaptopropionic acid is thus left, distillation is conducted under reduced pressure at 110° C. to 130° C. to remove the organic solvent and thereby obtain pure 3-mercaptopropionic acid. In the present step, since water in the reaction solution is separately removed and then distillation under reduced pressure is conducted, the solvent can be completely distilled through distillation under reduced pressure within a short time at a low temperature compared to the conventional method (Korean Patent Laid-open No. 10-2013-0087447) due to low boiling point of the solvent which should be distilled, so pure 3-mercaptopropionic acid can be obtained. In addition, since almost 100% of the prepared 3-mercaptopropionic acid is distilled in the n-butyl acetate layer, the yield can be increased to about 85% which is at least 10% higher than in the conventional method.

In accordance with the conventional method (Korean Patent Laid-open No. 10-2013-0087447), distillation under reduced pressure to obtain 3-mercaptopropionic acid generally requires high-temperature of about 140° C. and long time and as a result, a yield of about 70% is obtained. The reason for requiring distillation at a high temperature for a long time is that the organic solvent as well as a great amount of water should have been removed through distillation, since water cannot be separately removed from the reaction solution. However, according to the present invention, by first treating the reaction solution rendering preparation of 3-mercaptopropionic acid with n-butyl acetate, almost 100% of 3-mercaptopropionic acid can be separated into the organic layer, so that water, which has a high boiling point and requires a prolonged time for distillation, can be completely removed through layer-separation. Accordingly, since only the organic solvent has to be removed in the subsequent distillation step, pure 3-mercaptopropionic acid can be obtained by distillation at a low temperature for a short time. Furthermore, the yield can be greatly increased through complete layer-separation and damage to products resulting from treatment at a high temperature for a long time can be avoided. As the amount of product increases, the problem of deteriorated productivity, which the conventional method has, becomes more serious. In this regard, when 10 kg of 3-mercaptopropionic acid is prepared using the method disclosed in Korean Patent Laid-open No. 10-2013-0087447, it takes about 3 days, while when 10 kg of 3-mercaptopropionic acid is prepared using the method according to the present invention, it takes a short time of 5 hours or less.

A method for preparing a carboxylic acid ester compound having a mercapto group using the 3-mercaptopropionic acid obtained by the preparation method described above can be depicted by the following Reaction Scheme 2.

[Reaction Scheme 2]

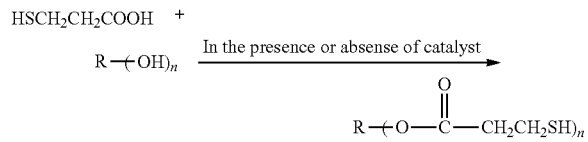

In the Reaction Scheme, R represents an alkylene or alkyl residue group and/or an alcohol residue group, and n is an integer of 2 to 4.

In Reaction Scheme 2 to obtain the carboxylic acid ester compound having a mercapto group, the reaction between the 3-mercaptopropionic acid according to the present invention and the compound having a monovalent or higher alcohol group can be carried out in the absence of a catalyst by adding an excess of 3-mercaptopropionic acid compared to an equivalent of an alcohol. Preferably, the amount of 3-mercaptopropionic acid used is 1 to 3-times, more preferably 1.5 to 2.5-times, of the equivalent of alcohol. It is not preferable that the amount of 3-mercaptopropionic acid used is lower than one-time, because the reaction speed is rapidly deteriorated, and it is not preferable that the amount of 3-mercaptopropionic acid used exceed 3-times, because the amount of product is deteriorated due to the capacity of the reactor and there is no further facilitation effect.

The compound having a monovalent or higher alcohol group according to the present invention is not particularly limited for the present invention, but is preferably a monovalent alcohol selected from methanol, ethanol, propanol, butanol, isopropanol, amyl alcohol, pentanol, hexanol, benzyl alcohol and the like, or an ethylene oxide (EO) or propylene oxide (PO) adduct thereof. The divalent alcohol is selected from ethylene glycol, diethylene glycol, triethylene glycol, tetraethylene glycol, propylene glycol, dipropylene glycol, tripropylene glycol, butanediol, pentanediol, hexanediol, bisphenol A and EO and PO adducts thereof. The trivalent or higher alcohol includes glycerol, trimethylol propane, pentaerythritol, dimers thereof and EO and PO adducts thereof and the like, and the compound having a monovalent or higher alcohol group may further include a compound having an alcohol group, in addition to the alcohol.

Water is produced as a reaction product of esterification of 3-mercaptopropionic acid with alcohol. In order to efficiently remove water, water can be removed to the outside of a system using a solvent such as toluene, cyclohexane or heptane through distillation under reduced pressure without using a solvent so as to promote the reaction.

After the reaction reaches a target level, mercaptopropionic acid is collected through distillation under reduced pressure such that the mercaptopropionic acid is adjusted to 0.3% or less to obtain the target product. There are conventional preparation methods using an acid catalyst, but these methods have problems of requiring an additional washing process since they offer final products with poor color. The present invention has an advantage of neither causing change in color nor requiring an additional washing process by not using any catalyst. It is deemed that the mercaptopropionic acid, which is added in an excessive amount, serves to some extent as a catalyst and some hydrochloric acid remains in the reaction of Reaction Scheme 1 in the process of continuously performing Reaction Schemes 1 and 2, thus facilitating reaction. In the case of using a catalyst, the catalyst is selected from those generally used for esterification and is preferably a strong acid catalyst, a Lewis acid catalyst, a catalyst using an enzyme or the like.

After obtaining the carboxylic acid ester compound having a mercapto group by the method described above, the obtained carboxylic acid ester compound having a mercapto group is mixed with a polyiso(thio)cyanate compound to prepare a thiourethane-based polymerizable composition according to the present invention. Also, the polymerizable composition is polymerized to obtain a thiourethane optical material according to the present invention.

A ratio of the carboxylic acid ester compound having a mercapto group and the polyiso(thio)cyanate compound used is not particularly limited for the present invention, but a ratio of SH groups to NCO groups is commonly within the range of 0.3 to 3.0, preferably 0.7 to 2.0, more preferably 0.8 to 1.3. When the molar ratio is within the range, impact strength and compressive strength of a resin obtained by curing a resin composition for optical lenses containing the carboxylic acid ester compound and the polyiso(thio)cyanate compound are improved, Abbe number is relatively high, and optical properties are thus excellent.

The polyiso(thio)cyanate compound is not particularly limited and may be a compound having at least one isocyanate and/or isothiocyanate group. Examples of the polyiso(thio)cyanate compound include one or more selected from aliphatic isocyanate compounds such as 2,2-dimethyl pentane diisocyanate, hexamethylene diisocyanate, 2,2,4-trimethylhexanediisocyanate, butane diisocyanate, 1,3-butadiene-1,4-diisocyanate, 2,4,4-trimethyl hexamethylene diisocyanate, 1,6,11-undecatriisocyanate, 1,3,6-hexamethylene triisocyanate, 1,8-diisocyanate-4-isocyanatomethyloctane, bis(isocyanatoethyl)carbonate, and bis(isocyanatoethyl)ether; cyclic isocyanate compounds such as isophorone diisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyl dimethylmethane isocyanate, and 2,2-dimethyl dicyclohexylmethane isocyanate; aromatic isocyanate compounds such as xylylene diisocyanate (XDI), bis(isocyanatoethyl)benzene, bis(isocyanatopropyl)benzene, bis(isocyanatobutyl)benzene, bis(isocyanatomethyl)naphthalene, bis(isocyanatomethyl)diphenylether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene diisocyanate, and hexahydrodiphenylmethane-4,4-diisocyanate; sulfur-containing aliphatic isocyanate compounds such as bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatopropyl) disulfide, bis(isocyanatomethylthio)methane, bis(isocyanatoethylthio)methane, bis(isocyanatoethylthio) ethane, bis(isocyanatomethylthio)ethane, and 1,5-diisocyanato-2-isocyanatomethyl-3-thiapentane; sulfur-containing aromatic isocyanate compounds such as diphenylsulfide-2,4-diisocyanate, diphenylsulfide-4,4-diisocyanate, 3,3-dimethoxy-4,4-diisocyanatodibenzylthioether, bis(4-isocyanatomethylbenzene)sulfide, 4,4-methoxybenzene thioethylene glycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxy diphenyldisulfide-4,4-diisocyanate, and 4,4-dimethoxydiphenyldisulfide-3,3-diisocyanate; sulfur-containing heterocyclic isocyanate compounds such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane. Any compound may be used alone or as a combination thereof so long as it has at least one isocyanate and/or isothiocyanate group. In addition, a halogenated product of the isocyanate compound, such as a chlorinated or brominated product of the isocyanate compound; an alkylated product of the isocyanate compound; an alkoxylated product of the isocyanate compound; a nitro-substituted product of the isocyanate compound; or a prepolymer-modified product of the isocyanate compound with polyalcohol or thiol, a carbodiimide-modified product of the isocyanate compound, a urea-modified product of the isocyanate compound or a biuret-modified product of the isocyanate compound; or a dimerization or trimerization product of the isocyanate compound. The polyiso(thio)cyanate compound may preferably include one or more selected from isophorone diisocyanate (IPDI), hexamethylene diisocyanate (HDI), dicyclohexylmethane diisocyanate (H12MDI), xylylene diisocyanate (XDI), 3,8-bis(isocyanatomethyl)tricyclo[5,2,1,02,6]decane, 3,9-bis(isocyanatomethyl)tricyclo[5,2,1,02,6]decane, 4,8-bis(isocyanatomethyl)tricyclo[5,2,1,02,6]decane, 2,5-bis(isocyanatomethyl)bicyclo[2,2,1]heptane, and 2,6-bis(isocyanatomethyl)bicyclo[2,2,1]heptane.

The polymerizable composition of the present invention may further include another polythiol compound. The polythiol compound which can be used in combination with the carboxylic acid ester compound having a mercapto group according to the present invention is not particularly limited and may be a thiol compound having two or more thiol groups in one molecule. For example, the other polythiol compound may include at least one selected from 4-mercaptomethyl-1,8-dimercapto-3,6-dithiaoctane, 2,3-bis(2-mercaptoethylthio)-3-propane-1-thiol; 2,2-bis(mercaptomethyl)-1,3-propanedithiol, bis(2-mercaptoethyl)sulfide, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl) sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio) ethane, bis(2-(2-mercaptoethylthio)-3-mercaptopropyl)sulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio) propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bis-pentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane and 2-(2,2-bis(mercaptodimethylthio)ethyl)-1,3-dithiane. Preferably, the thiol compound may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl)sulfide, 2-(2-mercaptoethylthio)-3-2-mercapto-3-[3-mercapto-2-(2-mercaptoethylthio)-propylthio]propylthio-propane-1-thiol, 2,2'-thiodiethanethiol, 4,14-bis(mercaptomethyl)-3,6,9,12,15-pentathiaheptadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritoltetrakis(3-mercaptopropionate), pentaerythritolmercaptoacetate, trimethylolpropane trismercaptopropionate, glycerol tri(mercaptopropionate), or dipentaerythritol hexamercaptopropionate or a combination thereof. In addition, compounds mixed with some of hydroxyl groups which are unreacted substances thereof may be included.

The polymerizable composition according to the present invention may further include an olefin compound as a reactive resin modifier for the purpose of controlling impact resistance, specific gravity and monomer viscosity in order to improve optical properties of the copolymer optical resin. In addition, the polymerizable composition according to the present invention may further include any additives such as internal release agents, UV absorbers, polymerization initiators, dyes, stabilizers, bluing agents and the like, if necessary. In addition, the polymerizable composition may further include a compound having a vinyl or unsaturated group, or a metal compound that can be copolymerized.

Among the additives, the UV absorber is preferably selected from benzophenone-based, benzotriazole-based, salicylate-based, cyanoacrylate-based and oxanilide-based UV absorbers and the like, the stabilizer (thermal stabilizer) may be selected from metal fatty acid salt-based, phosphorus-based, lead-based and organotin-based stabilizers and the like, the internal release agent includes fluorine-based nonionic surfactants, silicone-based nonionic surfactants, alkyl quaternary ammonium salt-based surfactants, acidic phosphoric acid ester-based surfactants and the like, the polymerization initiator may be selected from amine-based and organotin-based polymerization initiators and the like. The color controller may be a pigment or dye and the pigment may be an organic or inorganic pigment or the like. The dye may be an anthraquinone dispersion dye or the like. The antioxidant may be a phenol-, amine-, phosphorous- or thioester-based antioxidant or the like. These additives may be used alone or as a mixture of two or more thereof in order to improve properties of the optical lens.

In order to improve optical properties of the polymerizable composition for optical lenses, the stabilizer is preferably added in an amount of 0.01 to 5.00% by weight. When the content of the stabilizer is less than 0.01% by weight, the effect of improving stability is poor and when the content of the stabilizer exceeds 10.00% by weight, there are problems in that, during curing, polymerization defect proportion is high and the stability of cured substance is deteriorated.

The stabilizer may be a metal fatty acid salt-, phosphorus-, lead- or organotin-based stabilizer, or a mixture thereof. Preferably, the lens formed by using a phosphorous stabilizer can improve stability of the optical lens without deterioration in optical properties such as transparency, impact strength, heat resistance and polymerization yield.

The internal release agent may be selected from: fluorine-based non-ionic surfactants having a perfluoroalkyl group, a hydroxyalkyl group or a phosphoric acid ester group; silicone-based non-ionic surfactants having a dimethylpolysiloxane group, a hydroxyalkyl group or a phosphoric acid ester group; alkyl quaternary ammonium salts, that is, trimethylcetyl ammonium salts, trimethyl stearyl ammonium salts, dimethylethylcetyl ammonium salts, triethyldodecyl ammonium salts, trioctylmethyl ammonium salts and diethylcyclohexadodecyl ammonium salts; and acidic phosphoric acid ester or mixtures thereof. Preferably, the internal release agent may be acidic phosphoric acid ester and the acidic phosphoric acid ester may be isopropyl acid phosphate, diisopropyl acid phosphate, butyric acid phosphate, octyl acid phosphate, dioctyl acid phosphate, isodecyl acid phosphate, diisodecyl acid phosphate, tridecanol acid phosphate, bis(tridecanol acid)phosphate or the like or a mixture thereof. The embodiment according to the present invention shows that acidic phosphate ester-based ZELEC UN™ (Stepan Corp.) has the best release properties when the mold is removed from the lens. Preferably, the internal release agent may be used in an amount of 0.0001 to 10% by weight, preferably 0.005 to 2% by weight, with respect to the total weight of the reaction mixture because the release property of the mold from the lens is excellent and polymerization yield is also high. When the amount of the release agent is less than 0.005% by weight, the lens may be attached to the surface of the glass mold during removal of the formed optical lens from the glass mold, and when the amount of the release agent exceeds 2% by weight, the surface of the lens may be stained when the lens is removed from the glass mold during mold polymerization.

Furthermore, in order to improve abrasion resistance of the surface, a hard coating film may be placed on the outer surface of a cast molding resin. In addition, a primer layer is inserted between the surface of the resin and the hard coating film, thereby improving adhesivity of the resin to the hard coating film. In order to apply a hard coating agent to an outer surface of the resin to form the hard coating film on the surface, a resin, which has been completely cured and annealed, is first coated with a primer solution and is then coated with the hard coating agent by a commonly known method, for example, immersion, spin-coating, flow coating, spraying and other methods. In addition, an anti-reflective film can be formed on the surface of the cast molding resin so as to prevent surface reflection on the optical element and thereby improve transmission of visible light.

The optical material according to the present invention can be, for example, produced by injecting the polymerizable composition according to the present invention into a mold for lenses and curing the same. In addition, an epoxy compound, a thioepoxy compound, a compound having a vinyl or unsaturated group, a metal compound and the like, which can be copolymerized with the thiourethane resin composition, can be further incorporated during polymerization. The optical material, for example, the thiourethane-based lens, produced according to the present invention, can be produced by cast polymerization. Specifically, various additives and catalysts are dissolved in an isocyanate compound, a thiol compound is added thereto and defoaming under reduced pressure is conducted during cooling. Then, after an appropriate time, the resulting product is injected into the molded glass mold with a tape and cured for about 24 to 48 hours while heating from low temperature to high temperature.

EXAMPLE

Hereinafter, the present invention will be described in more detail with reference to specific examples. However, the examples will be provided only for illustration of the present invention and should not be construed as limiting the scope of the present invention.

Method for Analyzing Substances and Measuring Properties Thereof

1) Gas chromatography (GC) analysis: measured using an HP-1 column (J & W Scientific) with an Agilent Technologies 7890A GC System within the temperature range of 60° C. to 260° C. under heating conditions of 20° C./min.

2) HPLC measurement: measured using LC 20A (Shimazhu, Japan) and a C18 reverse phase column (Ace 5, 250×4.6 mm, ACE-121-2548, particle size: 5 μm) as a column, in the presence of a mixed solvent ($CH_3CN:H_2O=7:3$) as a solvent, at a flow rate of 1 mL/min at 195 nm of UV(λ), at 40° C. of an oven temperature.

3) Index of refraction and Abbe number: measured with DR-M4 model as a refractometer produced by Atago Co., Ltd.

4) APHA value: APHA value of a liquid material was measured using ColorQuest XE produced by Hunterlab Inc. The APHA values obtained by comparing the program having concentration data of the standard solution prepared by dissolving platinum and cobalt reagents, with the reagent solution, were determined to be measurement values. As measurement value decreased, color became better.

Synthesis of Mercaptopropionic Acid

Synthesis Example 1

3-Mercaptopropionic Acid (MPA-1)

A stirrer, a thermometer and a condenser were installed on a 1 L four-neck flask and $NaSH \cdot xH_2O$ (70%, 165.24 g, 2.65 moles) was charged in the flask and 160 g of water was added thereto and completely dissolved by stirring at 30° C. for 30 minutes. Then, while maintaining the temperature at 35° C., acrylonitrile (106.12 g, 2.00 moles) was slowly added dropwise. As heating occurred, the reaction proceeded. After the entirety of acrylonitrile was added, aging was conducted at 60° C. for 8 hours to obtain 2-sodium cyanoethanethiolate. The product was identified by GC analysis. After the starting material completely disappeared, 3-mercaptopropionitrile obtained by neutralizing the product, 2-sodium cyanoethanethiolate, was identified by GC analysis. After the reaction was completed, the temperature of the reactor was dropped to 10° C. and the reaction solution was neutralized while slowly dropwise adding concentrated hydrochloric acid at a temperature lower than 10° C. After the dropwise addition, the stirring was stopped, the supernatant layer, the nitrile compound, was layer-separated and the aqueous layer as a lower layer was removed to obtain the aqueous layer as the lower layer. Concentrated hydrochloric acid (35%, 208.3 g, 2.00 moles) was slowly added to the organic layer while stirring. The reaction proceeded at a temperature of 60° C. for one hour and the reaction solution was refluxed at 120° C. for 12 hours to obtain mercaptopropionic acid. The reaction was finished when GC analysis showed that the starting material, the nitrile compound, completely disappeared and 3-mercaptopropionic acid was produced. After the completion of the reaction, the temperature of the reaction solution was dropped and n-butyl acetate (1000 g) was added when the temperature reached 10° C. Subsequently, the mixture solution was neutralized with aqueous ammonia, filtered to remove the aqueous layer as the lower layer and distilled the organic (solvent) layer as the upper layer under reduced pressure (0.5 torr) at 120° C. to obtain 3-mercaptopropionic acid (180.43 g, 85%). The purity was 99.5% or more.

Synthesis Example 2

3-Mercaptopropionic Acid (MPA-2)

A stirrer, a thermometer and a condenser were installed on a 1 L four-neck flask and NaSH.xH$_2$O (70%, 177.79 g, 2.22 moles) was charged in the flask and 160 g of waster was added thereto and completely dissolved by stirring at 40° C. for 30 minutes. Then, while maintaining the temperature at 35° C., acrylonitrile (106.12 g, 2.00 moles) was slowly added. As heating occurred, the reaction proceeded. After the entirety of acrylonitrile was added, aging was conducted at 50° C. for 10 hours and stirring was conducted at the same temperature to obtain 2-sodium cyanoethanethiolate. 3-mercaptopropionitrile obtained by neutralizing the product, 2-sodium cyanoethanethiolate, was identified by GC analysis. After the reaction was completed, the temperature of the reactor was dropped to 10° C. and 3-mercaptopropionitrile produced by neutralization with concentrated hydrochloric acid was separated into the organic layer as the upper layer. The aqueous layer, the lower layer, was removed and concentrated hydrochloric acid was added to 3-mercaptopropionitrile, the upper layer. The reaction proceeded at a temperature of 60° C. for 2 hours and the reaction solution was refluxed at 120° C. for 12 hours to convert into 3-mercaptopropionic acid. The reaction was finished when the 3-mercaptoacetpnitrile was converted into 3-mercaptopropionic acid and the reaction product was cooled. Then, methyl isobutyl ketone (1000 g) was added and the mixture solution was then neutralized with aqueous ammonia, filtered to remove the separated aqueous layer and distilled under reduced pressure (0.5 torr) at 120° C. to obtain 3-mercaptopropionic acid (186.80 g, 88%). The purity measured by GC was 99.5% or more.

Comparative Synthesis Example 1

3-Mercaptopropionic Acid (MPA-3)

3-Mercaptopropionic acid was synthesized in accordance with the synthesis method disclosed in Korean Patent No. 10-0350658.

A stirrer, a thermometer and a condenser were installed on a 1 L four-neck flask and NaSH.H$_2$O (70%, 53.63 g, 0.67 moles) was charged in the flask, and 40 g of water was added thereto and was completely dissolved by stirring at 35° C. for 30 minutes. Then, while maintaining the temperature at 40° C. or less, acrylonitrile (66.00 g, 1.24 moles) was slowly added. A thiodipropionitrile-containing reaction solution was stirred at 40° C. for 10 minutes and acrylonitrile was slowly added dropwise. The reaction solution was heated to 45° C., 94.61 g (70%, 1.30 moles) of sodium hydrosulfide was rapidly added, and 24.80 g (50%, 0.31 moles) of sodium hydroxide was then slowly added. When sodium hydroxide was added, heating reaction occurred. Accordingly, the reaction temperature was maintained at 40° C. or less with a temperature controller. After the entirety of sodium hydroxide was added, the reaction solution was heated to 50 to 60° C. for 30 minutes. After 15 minutes, the reaction solution was converted into a homogeneous solution, the mixture solution was converted by acidification with 27% hydrochloric acid and refluxed at 100° C. under strong acid for 24 hours. However, GC showed that 3-mercaptopropionitrile was present together with 3-mercaptopropionic acid and reaction was not proceeded any more in spite of continuously conducting the reaction. Although the reaction solution was further refluxed for 24 hours, no reaction proceeded. Accordingly, the temperature of the reactor was dropped to room temperature, the product was extracted with methyl isobutyl ketone and the solvent was then removed and distillation was conducted at 140° C. under reduced pressure (0.5 torr) to obtain 3-mercaptopropionic acid. GC analysis of the product identified that 5% or more of 3-mercaptopropionitrile remained and was mixed with 3-mercaptopropionic acid. The amount of the obtained product was 78.98 g and was 75.03 g based on pure 3-mercaptopropionic acid, and the yield was 57%.

Synthesis of Carboxylic Acid Ester Having Mercapto Group

Synthesis Example 3

Trimethylolpropane tris(3-mercaptopropionate) (TMPMP-1)

A stirrer, a thermometer and a Dean-Stark apparatus were installed on a 1 L four-neck flask, 0.5 moles (67.08 g) of trimethylolpropane was added, 3 moles (318.42 g) of the 3-mercaptopropionic acid (MPA-1) obtained in Synthesis Example 1 was added thereto, 100 g of toluene was added as a solvent thereto, and the flask was installed in an oil bath and then heated. The temperature of the oil was elevated to 150° C. Water started to be produced around an inner temperature of 120° C. and reaction proceeded for 24 hours. Then, when production of water was almost not observed, the solvent and an excess of 3-mercaptopropionic acid were collected by distillation under reduced pressure. LC analysis results showed that the unreacted substance, trimethylolpropane, did not appear and the purity of the product was 88% and the amount of product obtained was 195.28 g. The index of refraction (nE) of the product was 1.518 and the color thereof was APHA 14, so that the product could be used as a polymerizable composition without separate washing or purification.

Synthesis Example 4

Trimethylolpropane tris(3-mercaptopropionate) (TMPMP-2)

A stirrer, a thermometer and a Dean-Stark apparatus were installed on a 1 L four-neck flask, 1 mole (134.17 g) of trimethylolpropane was added, 3 moles (318.42 g) of the 3-mercaptopropionic acid (MPA-2) obtained in Synthesis Example 2 was added thereto, 100 g of toluene was added as a solvent thereto, 2 g of p-toluenesulfonic acid was added as a catalyst, and the flask was installed in an oil bath and then heated. The temperature of the oil was elevated to 150° C. Water started to be produced around an inner temperature of 120° C. and reaction proceeded for 24 hours. Then, when production of water was almost not observed, the solvent and an excess of 3-mercaptopropionic acid were collected by distillation under reduced pressure. LC analysis results showed that the unreacted substance, trimethylolpropane, did not appear and the purity of the product was 88% and the amount of product obtained was 390.59 g. The index of refraction (nE) of the product was 1.519 and the color thereof was APHA 14, so that the product could be used as a polymerizable composition without separate washing or purification.

Synthesis Example 5

Pentaerythritol tetrakis(3-mercaptopropionate)(PETMP-1)

A stirrer, a thermometer and a Dean-Stark apparatus were installed on a 2 L four-neck flask, 1 mole (136.15 g) of pentaerythritol was added, 4 moles (424.56 g) of the 3-mercaptopropionic acid (MPA-1) obtained in Synthesis Example 1 was added thereto, 100 g of toluene was added as a solvent thereto, 2 g of p-toluenesulfonic acid was added as a catalyst and the flask was installed in an oil bath and then heated. The temperature of the oil was elevated to 150° C. Water started to be produced around an inner temperature of 120° C. and reaction proceeded for 24 hours. LC analysis results showed that pentaerythritol was not observed and the purity of the product was 87%, the remaining 3-mercaptopropionic acid was 0.2%, and the amount of product obtained was 478.88 g. The index of refraction (nE) of the product was 1.532 and the color thereof was APHA 10, so that the product could be used as a polymerizable composition without separate purification.

Synthesis Example 6

Pentaerythritol tetrakis(3-mercaptopropionate)(PETMP-2)

A stirrer, a thermometer and a Dean-Stark apparatus were installed on a 1 L four-neck flask, 0.5 moles (68.08 g) of pentaerythritol was added, 4 moles (424.56 g) of the 3-mercaptopropionic acid (MPA-2) obtained in Synthesis Example 2 was added thereto, 100 g of toluene was added as a solvent thereto and the flask was installed in an oil bath and then heated. The temperature of the oil was elevated to 150° C. Water started to be produced around an inner temperature of 120° C. and reaction proceeded for 24 hours. Then, when production of water was almost not observed, the solvent and an excess of 3-mercaptopropionic acid were collected by distillation under reduced pressure. LC analysis results showed that pentaerythritol was not observed and the purity of the product was 87%, the remaining 3-mercaptopropionic acid was 0.2%, and the amount of the target product obtained was 239.23 g. The index of refraction (nE) of the product was 1.531 and the color thereof was APHA 13, so that the product could be used as a polymerizable composition without separate washing or purification.

Comparative Synthesis Example 2

Trimethylolpropane tris(3-mercaptopropionate) (TMPMP-3)

A stirrer, a thermometer and a Dean-Stark apparatus were installed on a 1 L four-neck flask, 0.5 moles (67.08 g) of trimethylolpropane was added, 3 moles (318.42 g) of the 3-mercaptopropionic acid (MPA-3) obtained in Comparative Synthesis Example 1 was added thereto, 100 g of toluene was added as a solvent thereto, and the flask was installed in an oil bath and then heated. The temperature of the oil was elevated to 150° C. Water started to be produced around an inner temperature of 120° C. and reaction proceeded for 24 hours. Then, when production of water was almost not observed, the solvent and an excess of 3-mercaptopropionic acid were collected by distillation under reduced pressure. LC analysis results showed that the unreacted substance, trimethylolpropane, did not appear and the purity of the product was 81% and the amount of product obtained was 181.34 g. The index of refraction (nE) of the product was 1.515 and the color thereof was APHA 29.

Comparative Synthesis Example 3

Pentaerythritol tetrakis(3-mercaptopropionate)(PETMP-3)

A stirrer, a thermometer and a Dean-Stark apparatus were installed on a 1 L four-neck flask, 0.5 moles (67.08 g) of pentaerythritol was added, 3 moles (424.56 g) of the 3-mercaptopropionic acid (MPA-3) obtained in Comparative Synthesis Example 1 was added thereto, 100 g of toluene was added as a solvent thereto and the flask was installed in an oil bath and then heated. The temperature of the oil was elevated to 150° C. Water started to be produced around an inner temperature of 120° C. and reaction proceeded for 24 hours. Then, when production of water was almost not observed, the solvent and an excess of 3-mercaptopropionic acid were collected by distillation under reduced pressure and mercaptocarboxylic acid ester was washed with water and dried under reduced pressure. LC analysis results showed that pentaerythritol was not observed and the purity of the product was 80%, the remaining 3-mercaptopropionic acid was 0.3%, and the amount of the target product obtained was 215.78 g. The index of refraction (nE) of the product was 1.529 and the color thereof was APHA 28.

Production of Optical Lens

Example 1

(1) 24.09 g of isophorone diisocyanate, 18.23 g of hexamethylene diisocyanate and 57.67 g of TMPMP-1 were charged in a mix container, which could allow for vacuum defoaming, and 0.1 g of Zelec UN, 1.5 g of HOPBT, 20 ppm of HTAQ, 10 ppm of PRD and 0.1 g of BTC were added thereto while maintaining 15° C., followed by stirring for 20 minutes under a nitrogen stream to obtain a resin composition for lenses of eyeglasses, defoamed under reduced pressure of 0.1 torr or less for 90 minutes, charged with nitrogen and injected into a glass mold fixed with a polyester adhesive tape using a nitrogen pressure (dioptre: −5.00).

(2) The glass mold into which the resin composition for lenses of eyeglasses was injected was maintained in a forced-air oven at 35° C., heated to 40° C. for 3 hours, heated to 120° C. for 12 hours, maintained at 120° C. for 2 hours, cooled to 70° C. for 2 hours and cured by heating, and the mold was released from the solid substance to obtain an optical lens having a central thickness of 1.2 mm.

(3) After the optical lens obtained in (2) was processed to the diameter of 72 mm, ultrasonically washed with an alkali aqueous cleaning liquid and annealed at 120° C. for 2 hours.

(4) The lens obtained in (3) was surface-etched with a KOH 5% solution, impregnated in a hard liquid produced by Fine Coating Industry and then heat-cured, silicon oxide, zirconium oxide, ITO or a water film (fluoric resin) was deposited under vacuum on both surfaces of the lens to obtain a hard-coated and multi-coated lens for eyeglasses.

Examples 2 to 5

Compositions and lenses were produced in the same manner as in Example 1, except that the compositions shown in Table 1 were used. Physical properties were tested and results are shown in Table 1.

Comparative Examples 1 to 2

Compositions and lenses were produced in the same manner as in Example 1, except that the compositions shown in Table 1 were used. Physical properties were tested and results are shown in Table 1.

TABLE 1

| | | Examples | | | | | Comparative Examples | |
|---|---|---|---|---|---|---|---|---|
| | | 1 | 2 | 3 | 4 | 5 | 1 | 2 |
| Monomer composition (g) | TMPMP-1 (Synthesis Example 3) | 57.67 | | | | | | |
| | TMPMP-2 (Synthesis Example 4) | | 57.67 | | | | | |
| | TMPMP-3 (Comparative Synthesis Example 2) | | | | | | 57.67 | |
| | PETMP-1 (Synthesis Example 6) | | | 19.34 | 55.61 | | | |
| | PETMP-2 (Synthesis Example 7) | | | | | 55.61 | | |
| | PETMP-3 (Comparative Synthesis Example 8) | | | | | | | 55.61 |
| | GST | | | 32.01 | | | | |
| | IPDI | 24.09 | 24.09 | 17.59 | 25.27 | 25.27 | 24.09 | 25.27 |
| | HDI | 18.23 | 18.23 | 31.06 | 19.12 | 19.12 | 18.23 | 19.12 |
| Release agent (g) | Zelec UN | 0.1 | 0.1 | 0.1 | 0.1 | 0.1 | 0.1 | 0.1 |
| UV absorber (g) | HOPBT | 1.5 | 1.5 | 1.5 | 1.5 | 1.5 | 1.5 | 1.5 |
| Polymerization initiator (g) | BTC | 0.1 | 0.1 | 0.1 | 0.1 | 0.1 | 0.1 | 0.1 |
| Organic dye (ppm) | HTAQ | 20 | 20 | 20 | 20 | 20 | 20 | 20 |
| | PRD | 10 | 10 | 10 | 10 | 10 | 10 | 10 |
| Physical properties of lens | Index of refraction (nE, 20□) | 1.5579 | 1.5588 | 1.5980 | 1.5596 | 1.5601 | 1.5605 | 1.5979 |
| | Abbe number | 48 | 47 | 39 | 47 | 46 | 46 | 48 |
| | APHA | 14 | 14 | 13 | 12 | 10 | 29 | 31 |

<Abbreviations>
Monomers
  IPDI: isophorone diisocyanate
  HDI: hexamethylene diisocyanate
  TMPMP: trimethylolpropane tris(3-mercaptopropionate)
  PETMP: pentaerythritol-tetrakis(3-mercaptopropionate)
  GST: 2,3-bis(2-mercaptoethylthio)propane-1-thiol
Release Agent
  ZELEC UN: ZELEC UN™, the trademark of acidic phosphoric acid ester compound produced by Stepan Company
UV Absorber
  HOPBT: 2-(2'-hydroxy-5'-t-octylphenyl)benzotriazole
Organic Dye
  HTAQ: 1-hydroxy-4-(p-toluidine)anthraquinone
  PRD: perinone dye
Polymerization Initiator
  BTC: dibutyltin dichloride As can be seen from the results of Table 1, the optical lens which is obtained using the resin composition for optical lenses produced from the carboxylic acid ester compound having a mercapto group produced using the pure 3-mercaptopropionic acid according to the present invention exhibited excellent color. On the other hand, the optical lens obtained in Comparative Example was unsuitable as an optical lens due to poor optical lens composition.

INDUSTRIAL APPLICABILITY

According to the present invention, 3-mercaptopropionic acid can be obtained at a higher yield by an economic and easy process without breaking the product and a carboxylic acid ester compound having a mercapto group with excellent purity and color can be produced in an economic manner using the 3-mercaptopropionic acid. By using the carboxylic acid ester compound obtained by the present invention, in particular, for cheap thiourethane-based optical lenses, thiourethane-based optical lenses with excellent color can be produced. The thiourethane-based optical lens with excellent color obtained according to the present invention can be widely used in various fields, in particular, an eyeglass lens, a polarization lens or a camera lens, instead of a conventional optical lens.

The invention claimed is:
1. A method for preparing 3-mercaptopropionic acid comprising:
 (a) reacting acrylonitrile with sodium hydrosulfide to obtain 2-sodium cyanoethanethiolate;
 (b) neutralizing the 2-sodium cyanoethanethiolate by slowly dropwise adding concentrated hydrochloric acid at a temperature of 10° C. or less, removing an aqueous layer as a lower layer to allow an organic layer as upper layer to be left to obtain 3-mercaptopropionitrile; and
 (c) adding an acid to the 3-mercaptopropionitrile obtained as the organic layer and refluxing the resulting mixture to convert the 3-mercaptopropionitrile into 3-mercaptopropionic acid,
 dropping the temperature to 0 to 10° C., adding n-butyl acetate to the 3-mercaptopropionic acid to prepare a mixture solution, neutralizing the mixture solution with aqueous ammonia, and filtering the resulting solution to remove an aqueous layer as a lower layer and allow an organic layer as an upper layer to be left; and
 removing the solvent under reduced pressure from the organic layer and then distilling under reduced pressure at a temperature of 115° C. to 125° C. to obtain 3-mercaptopropionic acid.

2. The method according to claim 1, wherein, in the step (a), acrylonitrile is reacted with sodium hydrosulfide in a molar ratio of 1:0.9 to 1:1.5 to obtain the 2-sodium cyanoethanethiolate.

3. A method for preparing a carboxylic acid ester compound having a mercapto group comprising:
 obtaining 3-mercaptopropionic acid by the preparation method according to claim 1; and
 esterifying the obtained 3-mercaptopropionic acid with a compound having a monovalent or higher alcohol group to obtain the carboxylic acid ester compound having a mercapto group.

4. The method according to claim 3, wherein the 3-mercaptopropionic acid is reacted in an amount of 1 to 3 equivalents with respect to 1 equivalent of the compound having a monovalent or higher alcohol group.

5. A method for preparing a thiourethane-based polymerizable composition comprising:
 obtaining 3-mercaptopropionic acid by the preparation method according to claim 1;
 esterifying the obtain 3-mercaptopropionic acid with a compound having a monovalent or higher alcohol group to obtain a carboxylic acid ester compound having a mercapto group; and
 mixing the obtained carboxylic acid ester compound having a mercapto group with a polyiso(thio)cyanate compound to prepare the polymerizable composition.

6. The method according to claim 5, wherein the polyiso(thio)cyanate compound comprises at least one selected from the group consisting of isophorone diisocyanate (IPDI), hexamethylene diisocyanate (HDI), dicyclohexylmethane diisocyanate (H12MDI), xylylene diisocyanate (XDI), 3,8-bis(isocyanatomethyl)tricyclo[5,2,1,02,6]decane, 3,9-bis(isocyanatomethyl)tricyclo[5,2,1,02,6]decane, 4,8-bis(isocyanatomethyl)tricyclo[5,2,1,02,6]decane, 2,5-bis(isocyanatomethyl)bicyclo[2,2,1]heptane, and 2,6-bis(isocyanatomethyl)bicyclo[2,2,1]heptane.

7. The method according to claim 5, wherein the polymerizable composition further comprises another polythiol compound.

8. A method for producing a thiourethane-based optical material comprising:
 obtaining a thiourethane-based polymerizable composition by the preparation method according to claim 5; and
 polymerizing the obtained polymerizable composition to obtain the optical material.

* * * * *